United States Patent [19]

Govindan

[11] Patent Number: 5,011,937
[45] Date of Patent: Apr. 30, 1991

[54] TOLUENE SULFONATE SALTS OF 2-ALKYL IMIDAZOLINES

[75] Inventor: Cheruthur Govindan, Wadsworth, Ohio

[73] Assignee: PPG Industries, Inc., Pittsburgh, Pa.

[21] Appl. No.: 270,709

[22] Filed: Nov. 14, 1988

[51] Int. Cl.$^5$ .................. C07D 233/10; C07D 233/14; C08K 5/34
[52] U.S. Cl. ..................................... 548/354; 548/353; 524/94
[58] Field of Search ..................... 524/93, 94; 548/353, 548/354

[56] References Cited

U.S. PATENT DOCUMENTS

| | | | |
|---|---|---|---|
| 3,916,058 | 10/1975 | Vossos | 428/241 |
| 3,933,697 | 1/1976 | Fujii et al. | 260/2.5 A |
| 3,933,779 | 1/1976 | Baron | 260/93.5 |
| 4,118,525 | 10/1978 | Jones | 427/242 |
| 4,259,373 | 3/1981 | Demessemaekers et al. | 427/242 |
| 4,681,948 | 7/1987 | Worley | 548/319 |

OTHER PUBLICATIONS

Quaternary Imidazolium Compounds, Sawa, Natsu et al, CA: 70(3) 11699f, (Japanese Patent Publication 68/12354).

Antistatic Treatment of Synthetic Resins, Abe, Shoji, CA: 73(6) 26288g, (Japanese Patent Publication 70/03929).

Antihelminthic Preparation Based on Imidazole Derivative, CA: 80(6) 30718j (Japanese Patent Application 66/58918).

*Primary Examiner*—Joseph L. Schofer
*Assistant Examiner*—Mark D. Sweet
*Attorney, Agent, or Firm*—Irwin M. Stein

[57] ABSTRACT

Toluene sulfonate salts of 2-alkyl imidazolines, e.g., 2-undecyl-4,4,5,5-tetramethyl imidazoline, are described. These compounds may be used as internal or external antistatic agents for fibers, e.g., acrylic fibers, and synthetic polymers, e.g., polystyrene.

6 Claims, 1 Drawing Sheet

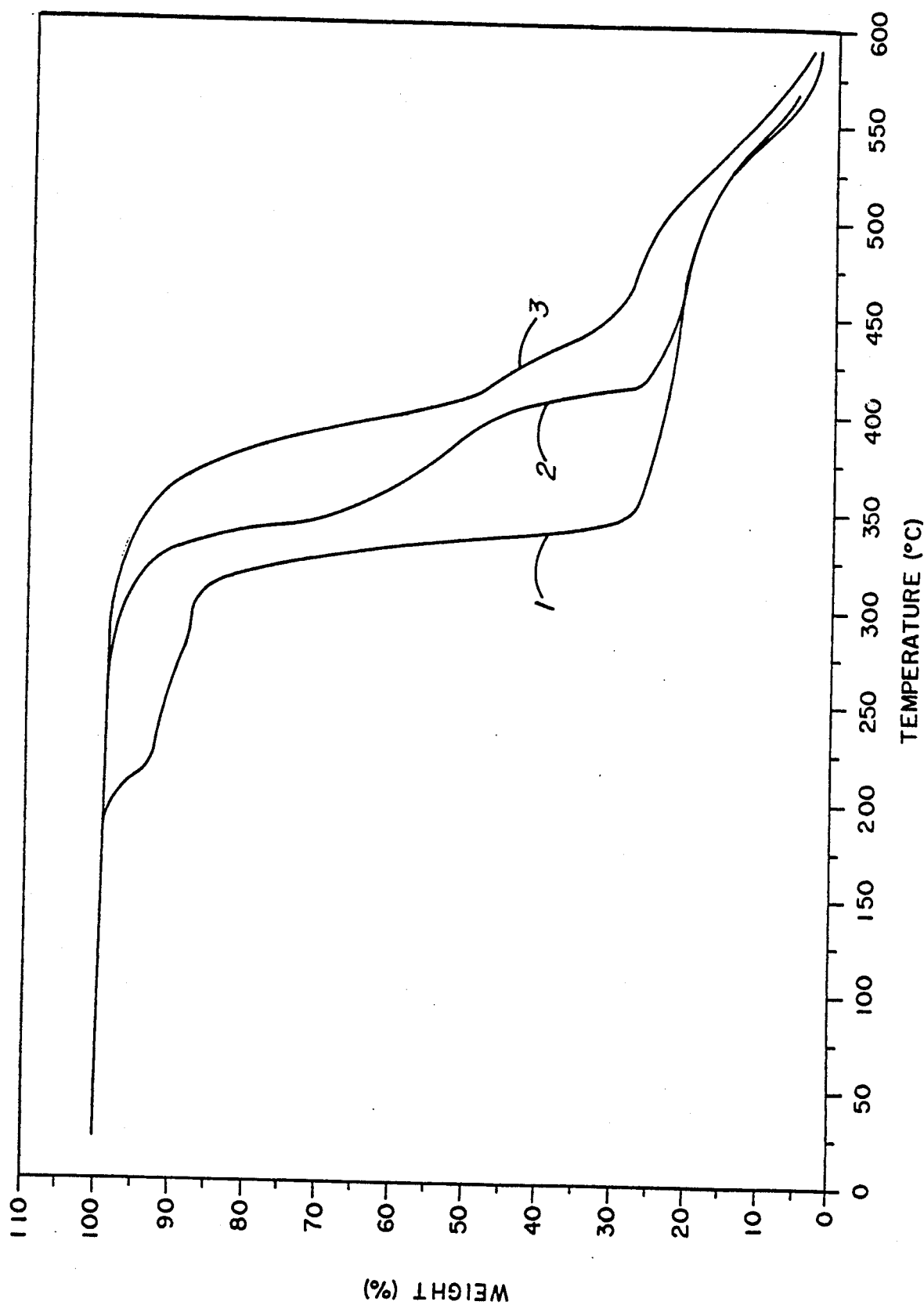

TOLUENE SULFONATE SALTS OF 2-ALKYL IMIDAZOLINES

DESCRIPTION OF THE INVENTION

The present invention relates to certain novel p-toluene sulfonate salts of 2-alkyl imidazolines and, more particularly, relates to the use of such compounds as internal and external antistatic agents for normally non-conducting organic materials, such as fibers and plastics. Still more particularly, the present invention relates to shaped articles of synthetic and naturally occurring organic polymers that have less than their normal tendency to accumulate static charges of electricity.

Organic materials, e.g., synthetic polymers are essentially electrical insulators, i.e., non-conductors of electricity. Articles prepared from such materials tend to develop electrostatic charges upon their surfaces when they are in a dry state and are subjected to frictional forces during their production and finishing, or during their handling and use. Such static charges are desirable for a number of reasons. For example, surface static charges readily attract dust and other contaminants, which are unsightly and difficult to clean. Often the contaminants or static charges themselves cause processing or handling problems. In certain cases, static charges may accumulate to a level where an unpleasant electrical shock is experienced when the article is handled. Fur(her, a high level of static charge on a molded part covering sensitive electronic equipment can damage such equipment.

Articles prepared from normally non-conducting organic materials, e.g., synthetic polymers such as plastics, may be surface treated with a finish containing an antistatic agent; however, surface treatments are less desirable than internally incorporated antistatic agents due to a wearing away of the applied finish. An antistatic agent that is incorporated within the article by, for example, blending the antistatic agent with the synthetic polymer prior to forming of the article, is susceptible to decomposition as a result of the high temperatures used to form the article, e.g., molding and extrusion. There is, therefore, a continuing need for more thermally stable antistatic agents that may be used with synthetic and naturally occurring materials.

It is an object of the present invention to provide novel antistatic agents for use internally or externally with formed normally non-conducting organic materials, e.g., synthetic polymers and other articles of manufacture, to lessen the accumulation of surface static charges on such materials.

In accordance with the present invention, there are provided certain alkyl imidazolinium p-toluene sulfonate salts that impart excellent antistatic properties to normally non-conducting materials, e.g., fibers and plastics, that tend to accumulate static charges of electricity when in a dry state. Such salts may be applied topically to the non-conducting material as part of a finish composition, or incorporated within the material, e.g., compounded with an organic synthetic polymeric material prior to it being formed into a shaped article.

BRIEF DESCRIPTION OF THE DRAWING

The sole figure is a graphical depiction of the thermograms of two imidazolinium para-toluene sulfonate compounds of the present invention and a 2-alkyl imidazolinium ethyl sulfate compound, which illustrates the comparative thermal stability of such compounds.

DETAILED DESCRIPTION OF THE INVENTION

It has now been discovered that certain P-toluene sulfonate salts of 2-alkyl imidazolines possess both markedly improved thermal stability and antistatic properties, i.e., electrostatic buildup and dissipation properties. Such properties may be measured by Federal Test Standard 101C, Method 4046, which measures the decay time for an applied charge of 5,000 volts. More particularly, the aforesaid salts may be represented by the following graphic formula:

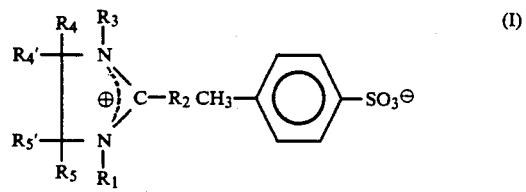

(I)

wherein $R_1$ and $R_3$ are each selected from the group consisting of hydrogen, $C_1$-$C_2$ alkyl, e.g., methyl and ethyl, and hydroxy ($C_2C_4$) alkyl, e.g., hydroxyethyl, hydroxypropyl and hydroxybutyl, $R_2$ is a $C_6$-$C_{22}$ alkyl, e.g., $C_8$-$C_{18}$ alkyl, and $R_4$, $R_4'$, $R_5$ and $R_5'$are each selected from the group consisting of hydrogen, $C_1$-$C_2$ alkyl, e.g., methyl and ethyl, hydroxy ($C_2$-$C_2$) alkyl, e.g., hydroxymethyl and hydroxyethyl, and pehnyl.

With respect to $R_2$, the term alkyl denotes a univalent, essentially saturated branched or straight chain alkyl group containing from 6 to 22 carbon atoms. Non-limiting examples of such alkyl groups are hexyl, isohexyl, heptyl, octyl, nonyl, decyl, undecyl, dodecyl, tridecyl, tetradecyl, pentadecyl, hexadecyl, heptadecyl, octadecyl, eicosyl soya, cocoyl and the like. When derived from naturally occurring materials, $R_2$ may be a mixture of alkyl groups and may contain a small amount of unsaturation.

Non-limiting examples of compounds depicted by graphic formula I include p-toluene sulfonate salts wherein $R_1$ through $R_5$ are selected from the substituents tabulated in Table 1.

TABLE 1

| Compound/ | $R_1$ | $R_2$ | $R_3$ | $R_4$ | $R_4'$ | $R_5$ | $R_5'$ |
|---|---|---|---|---|---|---|---|
| 1 | H | Undecyl | H | Me | Me | Me | Me |
| 2 | Me | Undecyl | H | Me | Me | Me | Me |
| 3 | Me | Undecyl | Me | Me | Me | Me | Me |
| 4 | HOEt | Undecyl | H | H | H | H | H |
| 5 | HOEt | Undecyl | Me | H | H | H | H |
| 6 | HOEt | Heptadecyl | Me | H | H | H | H |
| 7 | HOEt | Heptadecyl | Me | H | H | H | H |
| 8 | Me | Undecyl | Me | Me | Me | H | H |
| 9 | HOEt | Undecyl | Me | Me | Me | H | H |
| 10 | HOEt | Undecyl | HOEt | H | H | H | H |

KEY:
Me = Methyl
HOEt = Hydroxyethyl

The p-toluene sulfonate salt of Compound 1 in Table 1 may be named 2-undecyl-4,4,5,5-tetramethyl imidazolinium p-toluene sulfonate. Compound 3 may be named 2-undecyl-1,3,4,4,5,5-hexamethyl imidazolinium p-toluene sulfonate. Compound 5 may be names 2-undecyl-1-hydroxyethyl-3-methyl imidazolinium p-toluene sulfonate. Other p-toluene sulfonate salts of the compounds represented in Table 1 may be similarly named by utilizing the appropriate IUPAC radical name for the designated substituent.

Antistatic compounds of graphic formula I may be used to minimize the accumulation of static electricity by non-conducting articles, e.g., articles prepared from synthetic polymers, by applying to the surface of or incorporating within the article effective antistatic amounts of at least one of the compounds. Generally, the compounds of graphic formula I may be incorporated within the article in amounts of between about 0.5 and about 20 weight percent, preferably in amounts of between 2 and about 6 weight percent based on the weight of the dry, untreated article. When associated with a finish composition, the compounds of graphic formula I are generally present in amounts of from about 0.1 to about 2, e.g., 0.5 to 1 weight percent.

When compounded into a shaped article of a synthetic polymer, the antistatic compound will migrate or "bloom" to the surface of the article to provide an antistatic coating thereon. Such a coating is more permanent that an externally (topically) applied coating, since the latter can be removed by wear, wiping, washing, handling, movement in transit, etc. In contrast, if the migrated layer of an internally compounded antistatic agent should be removed during handling or processing, a new antistatic layer will bloom to the surface.

To apply the antistatic compound topically to the surface of an article, the antistatic compound may be dissolved or dispersed in water, lower alkanol, e.g., a $C_1$–$C_4$ alcohol, lubricating oil, polymeric coating, other organic solvent, etc., and the resulting "finish" containing the desired amount of antistatic compound applied to the surface using conventional coating techniques, e.g., spraying, dipping, wiping, etc., thereby to deposit an effective amount of antistatic agent on the surface of the article.

In general, the antistatic compounds of graphic formula I are thermally stable at temperatures in excess of 250° C. Moreover, they have excellent antistatic properties, i.e., they exhibit brief decay times. In contrast, ethyl sulfate salts of the imidazoline type can begin to decompose at about 180° C. The imidazolinium salts represented by graphic formula I show no significant decomposition up to 300° C. Further, even after having been heated at 240° C. for four hours, such compounds retain about 90 to 98 percent of their original weight whereas other quaternary ammonium compounds, e.g., quaternary ammonium p-toluene sulfonate salts lose from about 30 to 40 percent of their weight under such conditions.

Reference is made to the accompanying Figure, which is a graphical illustration of the thermograms of the three compounds:

I. 2-undecyl-1-hydroxyethyl-3-ethyl imidazolinium ethyl sulfate,
II. 2-undecyl-1-hydroxyethyl-3-methyl imidazolinium p-toluene sulfonate, and
III. 2-undecyl-1,3,4,4,5,5-hexamethyl imidazolinium p-toluene sulfonate.

As shown by the thermograms, compound I starts to decompose at about 180° C., whereas compounds II and III start to decompose at about 300° C. and about 350° C. respectively.

The compounds of graphic formula I may be solids, liquids, or low melting waxes at room temperature depending on the length of the $R_2$ alkyl substituent. Further, they do not form a hard residue even after prolonged heating. The residues remaining after heating are water soluble. Hence, they may be removed readily from equipment, such as rolls, used to apply an external antistatic finish. The opportunity to use antistatic agents that leave only water soluble residues after heating is important in the synthetic fiber industry where metal rollers that normally are hot during operation are used to apply an antistatic finish to the fiber. Any residue left on metal rollers by compounds of the present invention may be removed easily with a water washing, thereby reducing clean-up and equipment down time for removal of such residues. The excellent antistatic properties of the compounds of the present invention not only make their use cost effective, but since only small amounts need be incorporated into the material to be treated to attain an antistatic effect, it is not anticipated that such amounts will adversely affect the properties of the material with which the compounds are associated.

When antistatic compounds are incorporated internally into an article, the compound may be mixed in antistatic amounts with the synthetic polymer or other material used to form the article by conventional blending or mixing equipment, e.g., Banbury mixers or other rubber and plastic processing equipment, and the mixture formed into the article, e.g., by extrusion or other molding procedures. Alternatively, a master batch of the polymer and antistatic compound may be prepared and the master batch added in antistatic amounts to synthetic polymer that is used to form the article, thereby to provide the desired antistatic amount of antistatic compound within the article. A master batch may contain between about 10 and about 25 percent by weight of the antistatic compound.

The compounds of graphic formula I may be used with conventional synthetic polymers utilized to prepare formed articles. The compatibility of the antistatic compounds with a particular synthetic polymer may be readily determined by those skilled in the art. Antistatic compounds of graphic formula I may be used with a wide spectrum of substrate shapes, such as fibers (woven and nonwoven), sheets, films and molded or extruded articles. Such articles may be prepared from thermoplastic or thermosetting polymers or copolymers (including terpolymers).

Non-limiting examples of synthetic polymers from which formed articles may be prepared include polyolefins, such as polyethylene, polypropylene and polyisobutylene, styrene resins such as polystyrene, poly(chlorostyrene), styrene-acrylonitrile copolymers, poly(styrene-acrylonitrile-butadiene) terpolymers (ABS resins), and high impact polystyrene (HIPS), polyesters such as poly(methylacrylate), poly(methylmethacrylate) and poly(vinylacetate), ethylene glycolterephthalic acid polymers, polycarbonates, polyamides such as nylon and Kevlar ®-type polyamides, polyacetals such as poly(vinylbutyral), phenol-formaldehyde resins, polyurethanes, vinyl resins such as poly(vinyl chloride), poly(vinylidene chloride), polytrifluorochloroethylene, copolymers of vinyl chloride with vinyl acetate, vinylidene chloride or acrylonitrile, and poly(phenylene ether) resins. Mixtures of the aforesaid polymers may also be used, e.g., polymer alloys.

In addition, the compounds of graphic formula I may be used with natural materials or mixtures of natural and synthetic materials, e.g., rayon, acetate, rayon-cellulosic materials such as cellulose acetate-propionate, cellulose-butyrate, cotton, linen, jute, ramie, wool, mohair and glass, e.g., fiber glass and fiberglass insulation. The textile materials may take any form, including individual fibers, woven materials such as fabrics, cloth, carpets, rugs and upholstery, and non-woven materials such as felts, bats and mats. In the case of fiberglass strand or fiberglass insulation, the compounds of graphic formula I may be applied topically as a finish or as part of a sizing composition.

The compounds of graphic formula I may be readily prepared by reacting approximately equal molar amounts of the corresponding imidazoline and para-toluene sulfonate ester, e.g., methyl p-toluene sulfonate, in the presence of a solvent, e.g., water, lower alkanols, e.g., $C_1$–$C_4$ alkanols, acetonitrile, and acetone, at temperatures of from about 25° C. to about 150° C. Specific reaction temperatures will be determined by the boiling point of the solvent used. The reaction proceeds readily and results in a virtually stoichiometric yield. If an imidazoline reactant having no substituent on the nitrogen atoms is used, two moles of the para-toluene sulfonate ester, e.g., methyl p-toluene sulfonate, are used along with one mole of base, e.g., potassium carbonate.

The imidazoline can be prepared by methods known in the art such as by heating the corresponding diamine (II) with a monocarboxylic acid (III) or monocarboxylic acid ester at temperatures of from about 150° C. to about 250° C. The reaction provides excellent yields of the imidazoline. The imidazoline-forming condensation reaction may be illustrated as follows:

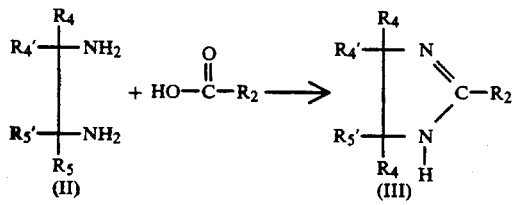

wherein $R_1$, $R_2$, $R_3$, $R_4$, $R_4'$, $R_5$ and $R_5'$ are as described hereinabove with respect to graphic formula I.

The present process is more particularly described in the following examples, which are intended as illustrative only since numerous modifications and variations therein will be apparent to those skilled in the art.

EXAMPLE 1

A one liter, three-necked flask equipped with magnetic stirrer, nitrogen inlet, thermometer and a ten-plate distillation column was charged with 140.0 grams (0.65 moles) of methyl laurate and 95.0 grams (0.82 moles) of 2,3-dimethyl-2,3-diaminobutane. The mixture was thoroughly purged with nitrogen and heated to 175° C. and maintained under reflux. The reaction temperature was maintained between 175° C. and 225° C. for 78 hours. At the end of this reaction period, gas chromatographic analysis of a sample of the reaction mixture indicated that less than 1 percent of methyl laurate remained unreacted. About 20 grams of distillate was collected during the reaction. The reaction mixture was evacuated to a pressure of 30 millimeters of mercury (4.0 kPa) and maintained at 200° C. until unreacted amine and unreacted methyl laurate had been removed. The residue (175.0 grams) remaining in the reaction flask was analyzed by gas chromatography and mass spectroscopy and found to be approximately 60 percent (by weight) of 2-undecyl-3,4,-4,5,5-pentamethyl imidazoline and 40 percent 2-undecyl-4,4,5,5-tetramethyl imidazoline.

EXAMPLE 2

205.0 grams of a mixture of 2-undecyl-tetra- and pentamethyl imidazolines prepared in the manner described in Example 1 were dissolved in 250 milliliters of acetone and heated to 45° C. 41.0 grams of powdered potassium carbonate were added to the resulting solution. Thereafter, a solution of 192.0 grams of methyl-p-toluene sulfonate in 60 milliliters of acetone was added dropwise and with stirring over a period of 45 minutes to the mixture. An exothermic reaction occurred and the mixture was maintained under reflux for 30 minutes after addition of all of the methyl-p-toluene sulfonate. The reaction mixture was filtered under nitrogen pressure and the filtrate stripped under vacuum to obtain 320.0 grams of a crude viscous liquid product. The crude product was dissolved in a mixture of 250 milliliters of diethyl ether and 30 milliliters of acetone and cooled in a freezer overnight. The crystals that separated from the solution were filtered, washed with diethyl ether and dried to obtain 265.0 grams of white crystals having a melting point of 43–45° C. The product, 2-undecyl-1,3,4,4,5,5-hexamethyl imidazolinium p-toluene sulfonate, was confirmed by nuclear magnetic resonance (NMR) and discharge ionization secondary mass spectrometry (DISIMS). Thermogravimetric analysis of the aforesaid recovered product was performed. The result is shown in the figure.

EXAMPLE 3

A one liter, three-necked flask equipped with thermometer, magnetic stirrer and heating mantle was charged with 230.0 grams of 2-(2-aminoethylamino) ethanol. The flask was flushed thoroughly with nitrogen and heated to 70° C. 400.0 grams of lauric acid was added slowly to the flask with vigorous stirring. After addition of lauric acid, the flask was evacuated to 200 millimeters of mercury pressure and heated to 140° C. After one hour, the temperature was raised to 220° C. and maintained at 100–200 millimeters of mercury for 1 hour. 23.0 grams of additional 2-(2-aminoethylamino) ethanol were added to the reaction flask and the reaction mixture stirred at 190° C. for 16 hours under a nitrogen pad. Excess 2-(2-aminoethylamine) ethanol in the reaction mixture was removed by distillation under reduced pressure. The residue was cooled to about 60° C. and dissolved in 800 milliliters of acetone and the resulting solution cooled in ice. The crystals that separated from the solution were filtered, washed with cold acetone and dried to obtain 325.0 grams of 2-undecyl-1-(2-hydroxyethyl) imidazoline. 265.0 grams of the imidazoline product was dissolved in 500 milliliters of warm acetone and several scoops of charcoal added to the solution. The mixture was stirred for 15 minutes and filtered. The solids were washed with 100 milliliters of acetone. The filtrates were combined and cooled to 10° C. with stirring in an ice bath. The crystals that separated were recovered by filtration, washed with cold acetone and dried. 213.0 grams of purified product were obtained.

EXAMPLE 4

The 213.0 grams of 2-undecyl-1-(2-hydroxyethyl) imidazoline product from Example 3 were dissolved in 250 milliliters of warm acetone. A solution of 147.10 grams of methyl-p-toluene sulfonate in 50 milliliters of acetone was added to the imidazoline solution over a period of 1 hour while maintaining the reaction temperature at 50–60° C. The resulting mixture was stirred overnight at 50° C. Thereafter, the solution was decolorized with charcoal, filtered and concentrated under vacuum to obtain 355.0 grams of the yellow viscous liquid product, 1-H-imidazolium, 4,5-dihydro-1-(2-hydroxyethyl)-3-methyl-2-undecyl p-toluene sulfonate.

The structure of the product was confirmed by DISIMS. Thermogravimetric analysis of the product was performed. The result is shown in the figure.

EXAMPLE 5

87.5 grams of Mazoline ® OA surfactant, which is 1-hydroxyethyl-2-oleyl imidazoline, was dissolved in 100 milliliters of acetone and 46.3 grams of methyl p-toluene sulfonate was added with stirring to the solution all at once. The temperature of the mixture increased to 60+° C. and acetone began to reflux. After about 5 minutes, the temperature of the mixture began to drop. Stirring of the reaction mixture at room temperature continued overnight. The solvent was stripped off in vacuo to obtain 130.0 grams of the product, 1-methyl-2-oleyl-3-hydroxyethyl imidazolinium p-toluene sulfonate.

EXAMPLE 6

50.0 grams of 2-heptadecyl-1-hydroethyl imidazoline, which was prepared by the reaction of stearic acid and aminoethylamino ethanol using the procedures described in Example 3, was stirred in 100 milliliters of acetone and a solution of 26.5 grams of methyl-p-toluene sulfonate in 50 milliliters of acetone was added to the imidazoline solution. The reaction mixture was stirred at 45° C. for 16 hours. Thereafter, the reaction medium was cooled in an ice bath to 5° C. and crystals of the unreacted imidazoline reactant that separated were removed by filtration. The filtrate was stripped in vacuo to obtain 75.0 grams of a thick paste product, i.e., 2-heptadecyl-1-hydroxyethyl-3-methyl imidazolinium p-toluene sulfonate.

EXAMPLE 7

Aqueous solutions containing 0.09 weight percent of each of the compounds corresponding to Examples 2, 4 and 5 were prepared. A 3.5 inch (8.9 cm)×5 inch (12.7 cm) swatch of an acrylic fiber obtained from Testfabrics Inc. was immersed in 100 grams of the aqueous solution being tested. Excess solution was squeezed from the swatch using an Atlas laboratory wringer. The swatch was air dried and then conditioned for 24 hours in a controlled humidity chamber at 15 percent relative humidity. This procedure was repeated for each of the test solutions. Electrostatic properties of the swatches were measured in accordance with Federal Test Standard 101C, Method 4046 by applying a charge of 5,000 volts to the acrylic fabric swatch and measuring the time in seconds required for the charge to decay to 0 volts with a static decay meter manufactured by Electrotech Systems.

Results are tabulated in Table 2.

TABLE 2

| COMPOUND, Example | 2 | 4 | 5 |
|---|---|---|---|
| Decay Time, Secs | 0.6 | 0.2 | 0.5 |

The data of Table 2 show that the compounds of Examples 2, 4 and 5 are excellent antistatic compounds—imparting excellent electrostatic properties to the acrylic fiber swatch.

EXAMPLE 8

Noryl ® N-190 modified poly(phenylene oxide) resin and various amounts of the antistatic compound corresponding to Example 2 were blended for 5 minutes in a Brabender mixer (100 rpm) at 210° C. Each of the resulting mixtures was compression molded at 440° F. (227° C.) into flat plaques about 55 mils thick. A 5 inch (12.7 cm) square disc cut from each of the plaques was conditioned for 24 hours in a controlled humidity chamber maintained at 15 percent relative humidity. The surface resistivity and electrostatic property (decay time) of each of the discs were measured using the test method described in Example 7. Results are tabulated in Table 3.

High impact polystyrene (HIPS-Mobil polystyrene 4226) and various amount of the antistatic compound corresponding to Example 2 were blended for 3 minutes in a Brabender mixer (100 rpm) at 210° C. Each of the resulting mixtures was compression molded at 420° F. (216° C.) into flat plaques about 55 mils thick. A 5 inch (12.7 cm) square disc cut from each of the plaques was conditioned for 24 hours in a controlled humidity chamber maintained at 15 percent relative humidity. The surface resistivity and electrostatic property (decay time) of each of the discs were measured using the test method described in Example 7. Results are tabulated in Table 3.

TABLE 3

| ANTI-STAT WT. % | NORYL RESIN | | HIPS RESIN | |
|---|---|---|---|---|
| | Decay Time | Resistivity | Decay Time | Resistivity |
| 0.0 | a. | $3.5 \times 10^{14}$ | a. | $5.6 \times 10^{13}$ |
| 0.5 | 1.6 | $3.4 \times 10^{11}$ | 2.7 | $7.3 \times 10^{11}$ |
| 1 | 0.42 | $8.6 \times 10^{10}$ | 1.6 | $1.5 \times 10^{11}$ |
| 2 | — | — | 3.3 | $4.7 \times 10^{11}$ |
| 3 | 1.3 | $1.9 \times 10^{11}$ | — | — |
| 5 | — | — | 0.2 | $1.5 \times 10^{12}$ |
| 6 | 0.3 | $5.8 \times 10^{10}$ | | |

Decay time reported in seconds.
Resistivity reported in ohms/square.
a. Resin would not accept charge.

EXAMPLE 9

Following the procedure of Example 8, 5 weight percent of the antistatic compound corresponding to Example 4 was compounded into high impact polystyrene and Noryl ® N-190 poly(phenylene oxide) resin. The electrostatic property of the disc prepared from the mixture measured. The decay time measured was about 0.6 seconds for the high impact polystyrene and 0.3 seconds for the Noryl ® N-190 resin.

EXAMPLE 10 (Comparative)

In accordance with the procedure of Example 8, various amounts of Hexcel ® 106G antistatic agent (which is reported to be the quaternary ammonium compound octyl methyl di(hydroxyethyl) ammonium-p-toluene sulfonate, were incorporated into the Noryl ® N-190 and HIPS resins described in Example 8. The decay time and surface resistivity measurements of discs prepared from such mixtures are tabulated in Table 4.

TABLE 4

| ANTISTAT Hexcel ® 106G WT. % | NORYL RESIN Decay Time | Resistivity | HIPS RESIN Decay Time | Resistivity |
|---|---|---|---|---|
| 0.5 | a. | $3.5 \times 10^{13}$ | a. | $7.5 \times 10^{13}$ |
| 1 | a. | $2.2 \times 10^{3}$ | a. | $2.7 \times 10^{13}$ |
| 2 | — | — | a. | $1 \times 10^{13}$ |
| 3 | 12.0 | $4.2 \times 10^{12}$ | — | — |
| 6 | 0.90 | $3.4 \times 10^{11}$ | — | — |

Decay time reported in seconds.
Resistivity reported in ohms/square.
a. Resin would not accept a charge.

The data of Table 4 shows that at low concentrations Hexcel ® 106G does not impart antistatic properties to a Noryl-type resin and does not impart antistatic properties to a HIPS-type resin at the concentrations measured.

EXAMPLE 11

A 500 milliliter, three-necked reaction flask equipped with a nitrogen inlet, ten plate Oldershaw column, distillation head condenser and thermometer was charged with 214.0 grams of methyl laurate and 132.0 grams of 2-methyl-1,2-propane diamine. The mixture was heated to 130° C. and maintained at between 130° C. and 140° C. for 18 hours. During that period, a small stream of nitrogen was introduced below the surface of the mixture and the reaction mixture stirred with a magnetic stirrer. Analysis of the reaction mixture showed that about 30 percent of the ester remained unreacted. Consequently, the reaction mixture was refluxed for a further 8 hours at 140° C.-150° C. and then overnight at 150° C.-160° C. Thereafter, the temperature was increased to 220° C. over 4 hours and held at that temperature for 4 hours. The reaction mixture was allowed to cool overnight and then was warmed to 100° C. and held at that temperature for 0.5 hour at a pressure of 1 millimeter of mercury (0.13 kPa). A total of 248.0 grams of 2-undecyl-5,5-dimethyl imidazoline was recovered.

25.2 grams of 2-undecyl-5,5-dimethyl imidazoline was dissolved in 100 milliliters of acetone and 13.8 grams of dry powdered potassium carbonate added to the solution. 37.3 grams of methyl-p-toluene sulfonate were added to the reaction mixture, which was stirred at room temperature over the weekend. The resultant mixture was filtered and the crystals washed with acetone. The filtrate was stripped yielding 32.7 grams of a light brown liquid product.

The brown liquid product was mixed with 60 milliliters of acetonitrile and 15.8 grams of methyl-p-toluene sulfonate and the mixture stirred at room temperature for 4 hours. The solvent was stripped in vacuo yielding 47.9 grams of crude product. The crude product was dissolved in 50 milliliters of acetone and 25 milliliters of diethyl ether and the solution cooled in a freezer. The crystals that separated were removed by filtration and discarded. The mother liquor was stripped to obtain 35.0 grams of 1,3,5,5-tetramethyl-2-undecyl-p-toluene sulfonate as a viscous syrup.

EXAMPLE 12 (Comparative)

7.8 grams of 2-undecyl-3-hydroxyethyl imidazoline was stirred in 50 milliliters of acetone and 4.4 grams of diethyl sulfate was added to the resulting solution. The reaction mixture was stirred at room temperature over a weekend. Thereafter, the reaction mixture was stripped on a rotovap to remove the acetone solvent. The residue was stripped further in vacuo to remove the last traces of solvent. The product, 2-undecyl-1-hydroxyethyl-3-ethyl-imidazolinium ethyl sulfate was recovered. Thermogravimetric analysis of the product was performed. The result is shown in the figure.

Although the present process has been described with reference to specific details of certain embodiments thereof, it is not intended that such details should be regarded as limitations upon the scope of the invention, except as and to the extent that they are included in the accompanying claims.

What is claimed is:

1. A compound represented by the graphic formula:

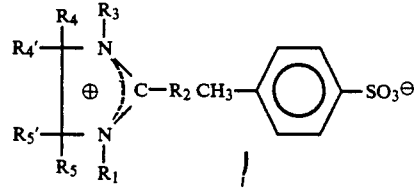

wherein $R^1$ and $R^3$ are each selected from the group consisting of hydrogen, $C_1-C_2$ alkyl and hydroxy ($C_2-C_4$) alkyl, $R_2$ is $C_6-C_{22}$ alkyl, and $R_4$, $R_4'$, $R_5$ and $R_5'$ are each selected from the group consisting of hydrogen, $C_1-C_2$ alkyl, hydroxy ($C_1-C_2$) alkyl and phenyl.

2. A compound according to claim 1 wherein $R_2$ is a $C_8-C_{18}$ alkyl, and $R_4$, $R_4'$, $R_5$ and $R_5'$ are each selected from the group consisting of hydrogen, $C_1-C_2$ alkyl, and hydroxy ($C_2-C_2$) alkyl.

3. A compound according to claim 1 wherein $R_1$ and $R_3$ are each selected from the group consisting of hydrogen, methyl and hydroxyethyl, $R_2$ is a $C_8-C_{18}$ alkyl, and $R_4'$, $R_5$ and $R_5'$ are each selected from the group consisting of hydrogen and methyl.

4. 2-undecyl-4,4,5,5-tetramethyl imidazolinium p-toluene sulfonate.

5. 2-undecyl-1,3,4,4,5,5-hexamethyl imidazolinium p-toluene sulfonate.

6. 2-undecyl-1-(2-hydroxyethyl)-3-methyl imidazolinium p-toluene sulfonate.

* * * * *

UNITED STATES PATENT AND TRADEMARK OFFICE
CERTIFICATE OF CORRECTION

PATENT NO. : 5,011,937
DATED : April 30, 1991
INVENTOR(S) : Cheruthur Govindan It is certified that error appears in the above-identified patent and that said Letters Patent is hereby corrected as shown below:

Column 10, claim 1, line 36, "$R^1$ and $R^3$" should be --$R_1$ and $R_3$--.

Column 10, claim 3, line 47, after "and" insert --$R_4$--.

Signed and Sealed this

First Day of February, 1994

*Attest:*

BRUCE LEHMAN

*Attesting Officer*     *Commissioner of Patents and Trademarks*